(12) United States Patent
Döring et al.

(10) Patent No.: US 7,973,191 B2
(45) Date of Patent: Jul. 5, 2011

(54) METHOD FOR THE PRODUCTION OF DIBENZ[C,E] [1,2]-OXAPHOSPHORIN DERIVATIVES, AMINO-DIBENZ[C,E] [1,2]-OXAPHOSPHORIN AND ALSO USE THEREOF

(75) Inventors: Manfred Döring, Wörth-Büchelberg (DE); Brigitte Lindner, Sargans (CH); Andreas Kaplan, Chur (CH)

(73) Assignee: EMS-Patent AG, Domat (CH)

( * ) Notice: Subject to any disclaimer, the term of this patent is extended or adjusted under 35 U.S.C. 154(b) by 0 days.

(21) Appl. No.: 12/539,972

(22) Filed: Aug. 12, 2009

(65) Prior Publication Data

US 2010/0069657 A1 Mar. 18, 2010

(30) Foreign Application Priority Data

Aug. 14, 2008 (CH) ...................................... 1281/08

(51) Int. Cl.
*C07F 9/02* (2006.01)
(52) U.S. Cl. ........................................................ 558/82
(58) Field of Classification Search ................ 558/82
See application file for complete search history.

(56) References Cited

U.S. PATENT DOCUMENTS

| 4,380,515 | A | * | 4/1983 | Rasberger et al. ............. 558/82 |
| 4,742,088 | A | | 5/1988 | Kim |
| 7,115,765 | B2 | | 10/2006 | Sprenger et al. |
| 2008/0167405 | A1 | | 7/2008 | Just et al. |

FOREIGN PATENT DOCUMENTS

| DE | 27 30 345 C3 | | 1/1980 |
| DE | 102 06 982 B4 | | 3/2004 |
| EP | 0 005 441 A1 | | 11/1979 |
| GB | 1256180 A | * | 12/1971 |
| GB | 1567849 A | | 5/1980 |
| JP | 54-138565 A2 | | 10/1979 |
| JP | 2001-323268 A2 | | 11/2001 |
| JP | 2002-284850 A2 | | 10/2002 |
| WO | WO 2006/084488 A1 | | 8/2006 |

* cited by examiner

*Primary Examiner* — Kamal A Saeed
*Assistant Examiner* — Nyeemah Grazier
(74) *Attorney, Agent, or Firm* — Leydig, Voit & Mayer, Ltd.

(57) ABSTRACT

The invention relates to general syntheses of (6H)-dibenz[c,e] [1,2]-oxaphosphorins which are substituted with nitrogen compounds on the phosphorus atom and comprising commercially available 6H-dibenz[c,e] [1,2]-oxaphosphorin-6-oxides. These nitrogen-containing (6H)-dibenz[c,e] [1,2]-oxaphosphorins can be used as reactive starting substances for further syntheses or as flameproofing agents or as stabilisers.

16 Claims, No Drawings

METHOD FOR THE PRODUCTION OF DIBENZ[C,E] [1,2]-OXAPHOSPHORIN DERIVATIVES, AMINO-DIBENZ[C,E] [1,2]-OXAPHOSPHORIN AND ALSO USE THEREOF

CROSS-REFERENCE TO A RELATED APPLICATION

This patent application claims the benefit of Swiss Patent Application No. 01281/08, filed Aug. 14, 2008, which is incorporated herein by reference.

The invention relates to general syntheses of (6H)-dibenz[c,e] [1,2]-oxaphosphorins which are substituted with nitrogen compounds on the phosphorus atom and comprising commercially available 6H-dibenz[c,e] [1,2]-oxaphosphorin-6-oxides. These nitrogen-containing (6H)-dibenz[c,e] [1,2]-oxaphosphorins can be used as reactive starting substances for further syntheses or as flameproofing agents or as stabilisers.

The single known production method for 6-alkylamino-(6H)-dibenz[c,e] [1,2]-oxaphosphorins is the conversion of 6-chloro-(6H)-dibenz[c,e] [1,2]-oxaphosphorins with amines:

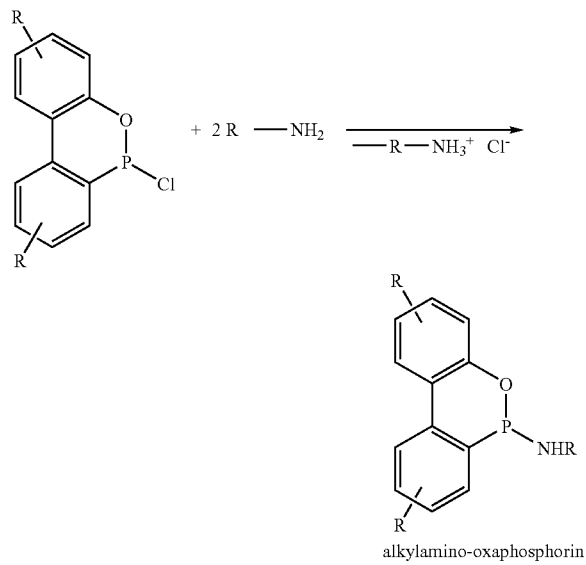

alkylamino-oxaphosphorin

This method is described in EP 0 005 441 B1 and JP 54138565.

In the known method for the synthesis of 6-alkylamino-(6H)-dibenz[c,e][1,2]-oxaphosphorins, 6-chloro-(6H)-dibenz[c,e] [1,2]-oxaphosphorins are required as starting substances. These chlorine-containing oxaphosphorins are intermediate products in the production of 6H-dibenz[c,e] [1,2]-oxaphosphorin-6-oxides, formula II. However they are very sensitive to hydrolysis and also otherwise not particularly stable and are therefore in general not isolated but converted immediately after production thereof into 6H-dibenz[c,e] [1,2]-oxaphosphorin-6-oxides II.

It is hence the object of the present invention to develop a method which makes possible the production of (6H)-dibenz[c,e] [1,2]-oxaphosphorin derivatives I which are substituted with nitrogen compounds on the phosphorus atom, starting from the commercially available but relatively inert 6H-dibenz[c,e] [1,2]-oxaphosphorin-6-oxides II, in a simple and economical way. In this method, no cost-intensive reagents should be required and no unusable by-products should be produced.

This object is achieved with respect to the method for the production of nitrogen-containing dibenz[c,e] [1,2]-oxaphosphorin derivatives I with the features of patent claim 1, with respect to the amino-dibenz[c,e] [1,2]-oxaphosphorins VII with the features of patent claim 13 and also with respect to the use of the products of the production method with the features of patent claim 15. The respective dependent claims thereby represent advantageous developments.

According to the invention, a method for the production of dibenz[c,e] [1,2]-oxaphosphorin derivatives of the general formula I is hence provided,

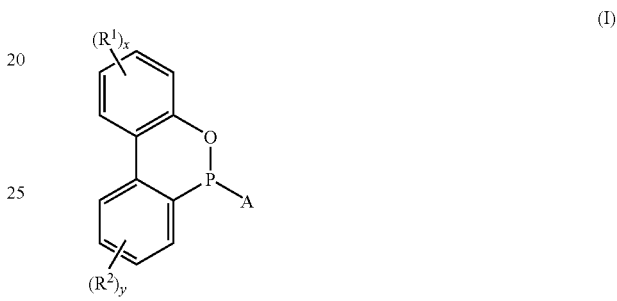

in which a 6H-dibenz[c,e] [1,2]-oxaphosphorin-6-oxide of the general formula II

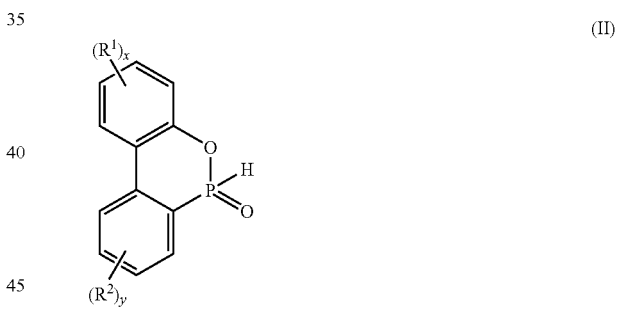

is made to react (α) with a primary amine, secondary amine, amine derivative and/or a hydrazine derivative of the general formula III

wherein in the general formulae I, II and III respectively, independently of each other, x and y are 0, 1, 2, 3 or 4, $R^1$ and $R^2$ are the same or different and mean hydrogen, linear or branched $C_1$-$C_{22}$ alkyl radicals, linear or branched $C_1$-$C_{22}$ oxa radicals, alkylsulphonyl radicals, arylsulphonyl radicals, thioaryl radicals, thioalkyl radicals, linear or branched $C_3$-$C_{22}$ alkenyl radicals, linear or branched $C_3$-$C_{22}$ alkinyl radicals, linear or branched $C_1$-$C_{22}$ hydroxyalkyl radicals, linear or branched $C_3$-$C_{22}$ alkoxycarbonylalkyl radicals, $C_3$-$C_{12}$ cycloalkyl radicals, $C_6$-$C_{14}$ aryl radicals, $C_7$-$C_{22}$ aralkyl radicals, $C_7$-$C_{22}$ alkylaryl radicals, a possibly substituted piperidin-4-yl group and/or halogen atoms,

A is a primary amine radical, a secondary amine radical substituted in a similar or mixed manner, a heterocyclic amine radical or a hydrazine derivative radical, and

Z is hydrogen, lithium, sodium or potassium.

Alkylsulphonyl- or arylsulphonyl radicals are also termed —$SO_2$-alkyl- or —$SO_2$-aryl radicals.

There are understood by oxa radicals radicals with an oxygen atom as bridge atom, such as e.g. —O-alkyl or —O-aryl.

The preparation of nitrogen-containing (6H)-dibenz[c,e][1,2]-oxaphosphorin derivatives I by direct conversion of amines and/or hydrazines with commercially available 6H-dibenz[c,e][1,2]-oxaphosphorin-6-oxides II has been unknown to date.

In the new synthesis, the commercially available 6H-dibenz[c,e][1,2]-oxaphosphorin-6-oxide II can be begun with. The conversion is effected by direct reaction with the corresponding amines and/or hydrazines or the derivatives thereof and requires no further reagents.

In the present invention, it is likewise advantageous that the process starts with a pentavalent phosphorus compound instead of a trivalent chlorinated phosphorus compound, as is required in the state of the art. In this respect, the reaction can be controlled specifically and by-products, as occur in general with increasing frequency in trivalent phosphorus chemistry, can be avoided.

The amine radical and/or hydrazine derivative radical (radical A of formula I or formula III) can contain up to 6 nitrogen atoms.

A preferred amine radical A of formula I or formula III is represented by the general formula IV,

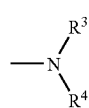

(IV)

$R^3$ meaning hydrogen, linear or branched $C_1$-$C_{22}$ alkyl radicals, linear or branched $C_1$-$C_{22}$ oxa radicals, alkylsulphonyl radicals, arylsulphonyl radicals, thioaryl radicals, thioalkyl radicals, linear or branched $C_3$-$C_{22}$ alkenyl radicals, linear or branched $C_3$-$C_{22}$ alkinyl radicals, linear or branched $C_1$-$C_{22}$ hydroxyalkyl radicals, linear or branched $C_3$-$C_{22}$ alkoxycarbonylalkyl radicals, $C_3$-$C_{12}$ cycloalkyl radicals, $C_6$-$C_{14}$ aryl radicals, $C_7$-$C_{22}$ aralkyl radicals, $C_7$-$C_{22}$ alkylaryl radicals or a possibly substituted piperidin-4-yl group, and $R^4$ meaning linear or branched $C_1$-$C_{22}$ alkyl radicals, linear or branched $C_1$-$C_{22}$ oxa radicals, alkylsulphonyl radicals, arylsulphonyl radicals, thioaryl radicals, thioalkyl radicals, linear or branched $C_3$-$C_{22}$ alkenyl radicals, linear or branched $C_3$-$C_{22}$ alkinyl radicals, linear or branched $C_1$-$C_{22}$ hydroxyalkyl radicals, linear or branched $C_3$-$C_{22}$ alkoxycarbonylalkyl radicals, $C_3$-$C_{12}$ cycloalkyl radicals, $C_6$-$C_{14}$ aryl radicals, $C_7$-$C_{22}$ aralkyl radicals, $C_7$-$C_{22}$ alkylaryl radicals or a possibly substituted piperidin-4-yl group.

Alternately or additionally, hydrazine derivative radicals can likewise be used advantageously, the radical A (of formula I or formula III) preferably representing here a radical of the general formula V,

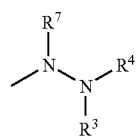

(V)

$R^3$ and $R^4$ having the above-indicated meaning and $R^7$ meaning hydrogen, linear or branched $C_1$-$C_{22}$ alkyl radicals, linear or branched $C_1$-$C_{22}$ oxa radicals, alkylsulphonyl radicals, arylsulphonyl radicals, thioaryl radicals, thioalkyl radicals, linear or branched $C_3$-$C_{22}$ alkenyl radicals, linear or branched $C_3$-$C_{22}$ alkinyl radicals, linear or branched $C_1$-$C_{22}$ hydroxyalkyl radicals, linear or branched $C_3$-$C_{22}$ alkoxycarbonylalkyl radicals, $C_3$-$C_{12}$ cycloalkyl radicals, $C_6$-$C_{14}$ aryl radicals, $C_7$-$C_{22}$ aralkyl radicals, $C_7$-$C_{22}$ alkylaryl radicals or a possibly substituted piperidin-4-yl group.

The reaction according to the invention can be implemented without solvents but also in an inert aprotic solvent, the solvent being selected here in particular from the group comprising ligroin, benzene, toluene, xylene, hexane, cyclohexane, dimethylformamide, dimethylacetamide, sulpholane, acetonitrile, dioxane, di-n-butylether, 1,2-dichloroethane, dimethylsulphoxide, acetic acid ester, methylethylketone, nitrobenzene, nitromethane, tetrohydrofuran, chloroform, trichlorethane and/or mixtures hereof.

The mixture ratio, in which the amine- and/or hydrazine derivative of the general formula III can be used in the molar material quantity ratio to the oxaphosphorin oxide of formula II, hereby is for example from 1:1 to 50:1, preferably 1:1 to 20:1, particular preferred 1:1 to 10:1.

The reaction components of the general formulae II or III can be added respectively in several portions to the reaction mixture.

Preferably, the 6H-dibenz[c,e][1,2]-oxaphosphorin-6-oxide of formula II is used as powder. The average particle diameter of the powder thereby is 0.1 to 0.4 mm, preferably 0.2 to 0.3 mm.

In a further advantageous embodiment, the reaction is implemented at temperatures between 10 and 200° C., preferably between 20 and 120° C.

The crude product is purified at 115 to 160° C., preferably at 125 to 145° C., by distillation at a pressure of less than 4 mbar, preferably less than 1 mbar.

In the reaction (α) according to the invention according to claim 1, it is possible that an open-chain by-product of the general formula VI is produced

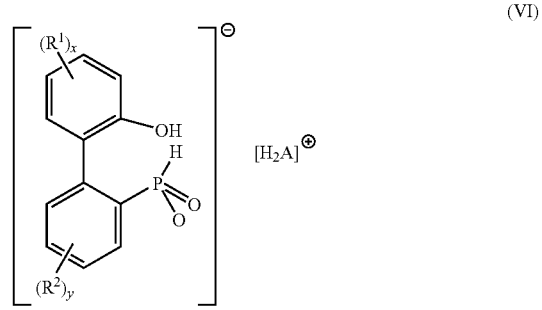

(VI)

$R^1$, $R^2$, A, x and y having the above-indicated meaning. It is hereby advantageous in particular that this by-product is separated from the reaction mixture, e.g. by filtration or centrifugation, and the oxaphosphorin oxide of formula II is recovered therefrom by thermolytic decomposition (reaction (β)) and also the compound of formula III by water splitting.

It is hereby advantageous if the thermolysis is implemented at temperatures between 80 and 280° C., preferably between 100 and 200° C.

It is likewise thereby of advantage if the thermolysis is implemented at reduced pressure, in particular at pressures less than 100 mbar, preferably less than 15 mbar, particularly preferred at 0.01 to 10 mbar. There is hereby understood by reduced pressure a pressure less than normal pressure.

In particular from economic and ecological points of view, it is thereby advantageous if at least the oxaphosphorin oxide of formula II which is produced during the thermolysis (reaction (β)), preferably both the oxaphosphorin oxide of formula II produced during the thermolysis and the nitrogen compound of formula III, is supplied again to the method as educts.

If the two reactions (α) and (β) are combined, the water is the only by-product of the process.

According to the invention, a nitrogen-containing dibenz[c,e] [1,2]-oxaphosphorin of the general formula I is also provided,

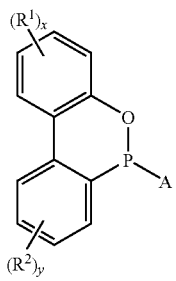

(I)

$R^1$, $R^2$, x, y and A having the above-indicated meaning.

In a preferred variant, a nitrogen-containing dibenz[c,e] [1,2]-oxaphosphorin of the general formula VII is provided,

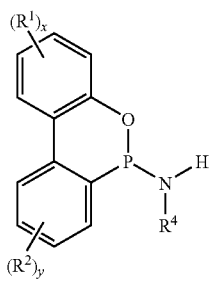

(VII)

$R^1$, $R^2$, $R^4$, x and y having the above-indicated meaning.

This nitrogen-containing dibenz[c,e] [1,2]-oxaphosphorin thereby emerges from the reaction of a 6H-dibenz[c,e] [1,2]-oxaphosphorin-6-oxide II with a primary amine IV and can be produced in particular according to the above-described method.

The nitrogen-containing dibenz[c,e] [1,2]-oxaphosphorins according to formula I or formula VII are used as flameproofing agents and/or stabilisers against damage due to the effect of oxygen, light, warmth and/or heat for plastic materials and/or elastomers.

The present invention is explained in more detail with reference to the subsequent embodiments, reaction equations and examples without restricting the invention to the special parameters shown there.

Schematic Example of the Reactions (α) and (β)

The production of the (6H)-dibenz[c,e] [1,2]-oxaphosphorins substituted with nitrogen compounds on the phosphorus atom can be effected for example by the conversion of commercially available 6H-dibenz[c,e] [1,2]-oxaphosphorin-6-oxides II with primary aliphatic amines IIIω, inert, aprotic solvents being used as reaction medium.

The first reaction (α) thereby comprises the conversion of 6H-dibenz[c,e] [1,2]-oxaphosphorin-6-oxides II with a primary aliphatic amine (IIIω), half being the 6-alkylamino-(6H)-dibenz[c,e] [1,2]-oxaphosphorins Iω and half the corresponding alkylammonium salts of 6H-dibenz[c,e] [1,2]-oxaphosphorin-6-oxides VIω:

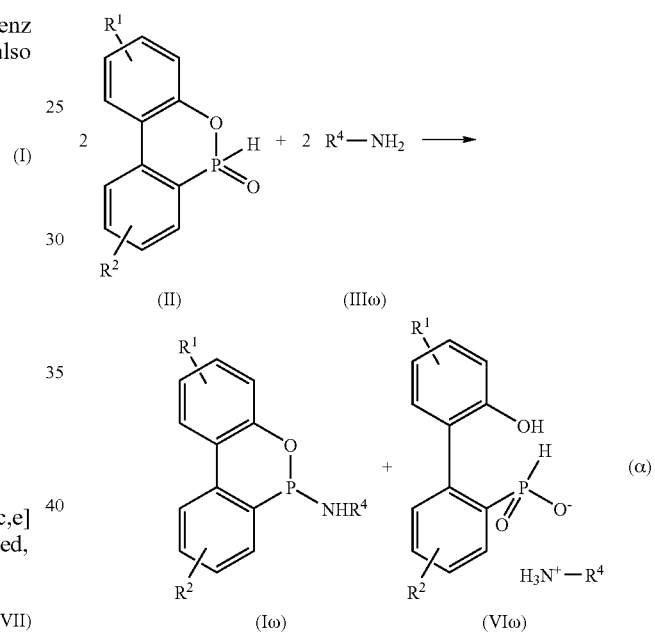

$R^1$, $R^2$ and $R^4$ having the above-indicted meaning.

In the second reaction (β), a thermolysis, the jointly produced alkylammonium salts of 6H-dibenz[c,e] [1,2]-oxaphosphorin-6-oxides VIω corresponding to equation (β) are decomposed by heating in a vacuum. The 6H-dibenz[c,e] [1,2]-oxaphosphorin-6-oxides II and also the primary amine are thereby recovered:

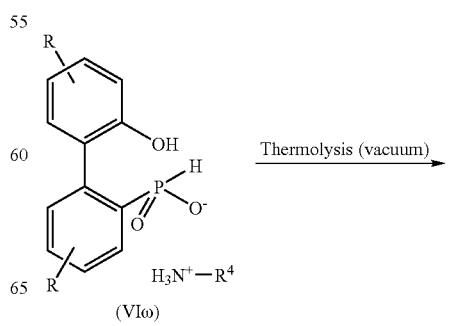

(VIω)

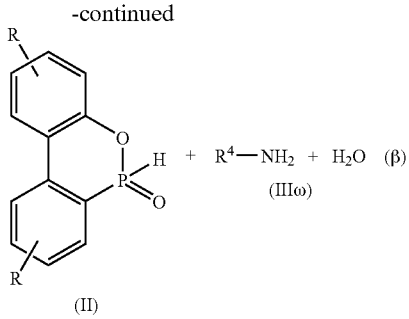

$R^1$, $R^2$ and $R^4$ having the above-indicated meaning.

These materials (II or IIIω)) can be used again for the synthesis of 6-alkylamino-(6H)-dibenz[c,e] [1,2]-oxaphosphorins Iω. If the recovery of the starting substances is applied, it is possible to convert the 6H-dibenz[c,e] [1,2]-oxaphosphorin-6-oxides II completely into 6-alkylamino-(6H)-dibenz[c,e] [1,2]-oxaphosphorins Iω, and water alone is produced as waste product. The entire conversion can be described in this case by equation (γ):

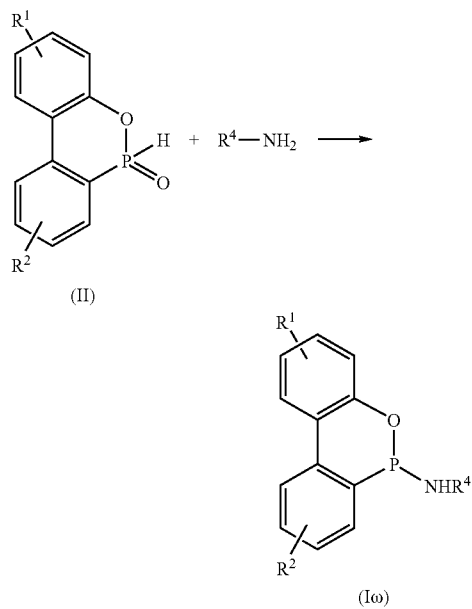

TEST EXAMPLES

1. 6-N(1-propylamino)-(6H)-dibenz[c,e] [1,2]-oxaphosphorin Ia from 6H-dibenz[c,e] [1,2]oxaphosphorin-6-oxide IIa

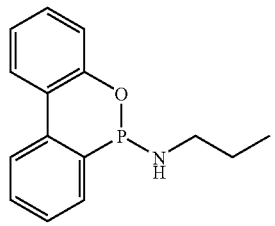

In a 4-litre flask which is equipped with a sturdy agitator, a reflux cooler, a device for adding solid materials, an inert gas transfer pipe, a thermometer and also with a heating bath, a mixture of 1600 ml n-heptane and 9.0 mol (532 g, 740 ml) 1-propylamine (IIIa) is heated to 45° C. Then 0.267 mol (57.64 g) 6H-dibenz[c,e] [1,2]-oxaphosphorin-6-oxide IIa are added with vigorous agitation. This starting substance is used as powder which should have an average particle diameter of approx. 0.25 mm. After the first addition of solid material, the temperature is maintained for another 45 min at 45° C., this being agitated vigorously and the particles being converted into viscous drops. Then 4 g seed crystals (1-propylammonium-(2-hydroxy-biphenyl-2-yl)-phosphinate; VIa) are added. Subsequently, the reaction mixture is heated within 10 min to 52 to 53° C., maintained at this level for a further 10 min and subsequently cooled to 47° C. Whilst agitation takes place vigorously in addition, a grainy solid material is produced from the droplets. After 45 min at 47° C., the second portion of the starting substance IIa (0.267 mol; 57.64) is added and also the third or fourth addition of solid material is effected after respectively 45 min (respectively 0.267 mol or 57.64 g). The remaining four portions IIa are added at intervals of respectively 35 min (respectively 0.267 mol or 57.64 g), the temperature being increased gradually to 53° C. In this 2 h 20 min, also a further 3.0 mol (177 g; 246 ml) 1-propylamine (IIIa) are added in drops. The obtained suspension is agitated for another 2 h at 53° C. and also for 5 h at approx. 20° C. Subsequent thereto, the excess 1-propylamine (IIIa) is distilled off. Then 300 ml n-heptane are added and this is agitated for a further hour without supply of heat. Thereafter, the grainy solid material VIa is filtered off with the help of a glass frit with the exclusion of moisture and the filter cake is rinsed twice with respectively 150 ml n-heptane. Now the combined filtrates are transferred into a distillation apparatus and the solvent is distilled off. A viscous, light yellow liquid is obtained as distillation residue, which comprises up to 98 to 99% by mol of the product Ia. This crude product is distilled in a fine vacuum (0.1 mbar). At 135 to 138° C. the compound Ia distilled as a colourless, oily liquid. Yield: 247 g or 45% of the theoretical quantity.

$^1$H-NMR (DMSO-$d_6$, 250 MHz): δ=0.52-0.63 (t, 3H); 0.97-1.24 (m, 2H); 2.43-2.60 (m, 2H); 4.72-4.83 (q, 1H); 7.06-7.20 (m, 2H); 7.28-7.38 (m, 1H); 7.40-7.50 (m, 1H); 7.50-7.60 (m, 2H); 8.0-8.09 (m, 2H); $^{13}$C-NMR (DMSO-$d_6$, 63 MHz): δ=11.29; 25.70; 25.75; 46.55; 46.69; 120.73; 122.80; 123.33; 123.49; 123.71; 125.39; 127.62; 127.82; 129.84; 130.60; 130.71; 131.42; 133.14; 133.23; 133.54; 133.58; 150.94; 151.07; $^{31}$P-NMR (DMSO-$d_6$): δ=79.18.

Details of the shift δ respectively in ppm.

The solid material VIa can be decomposed by heating in a vacuum, the starting substances IIa and 1-propylamine being recovered and in addition water being produced. This is described in the following.

Recovery of 6H-dibenz[c,e] [1,2]-oxaphosphorin-6-oxide IIa from the filter cake by thermolysis The poorly soluble solid material VIa occurring during the synthesis of 6-propylamino-(6H)-dibenz[c,e] [1,2]-oxaphosphorin Ia is heated in the course of 45 min to 165° C., the pressure being reduced slowly to approx. 5 mbar. Soon after the thermolysis of the compound begins, the solid material melts and the agitation is begun in order to restrict the foaming-up. The compounds 1-propylamine (IIIa) and water produced during the thermolysis are condensed in a vacuum trap. The melt is agitated for another 90 min at 165° C. and 5 mbar in order to complete the decomposition process and, after removing the vacuum, it is poured into a metal dish. During cooling, it solidifies to form a compact solid material which is initially ground roughly and subsequently ground to form a powder. The thus obtained white powder comprises up to 99% by mol 6H-dibenz[c,e] [1,2]-oxaphosphorin-6-oxide IIa and can be used without further purification for the synthesis of 6-N(1-propylamino-(6H)-dibenz[c,e] [1,2]-oxaphosphorin Ia.

2. 6-N(1-butylamino)-(6H)-dibenz[c,e] [1,2]-oxaphosphorin Ib from 6H-dibenz[c,e] [1,2]-oxaphosphorin-6-oxide IIa

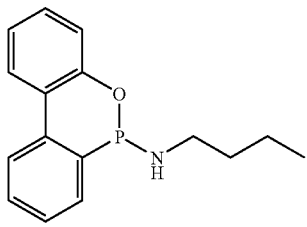

(Ib)

In a 500 ml flask filled with nitrogen or argon, which is equipped with an agitator, a reflux cooler with an inert gas transfer pipe, a thermometer and also with a heating bath, there are added in succession 0.2 mol (43.23 g) 6H-dibenz[c,e] [1,2]-oxaphosphorin-6-oxide IIa and also 0.6 mol (44 g; 59 ml) 1-butylamine (IIIb). The two substances initially form a pulp-like suspension which is gradually heated and can then be agitated. In the course of approx. 1 hour, the solid starting substance added as powder is dissolved and a yellow, clear liquid is produced. After 75 min without external supply of heat, the temperature is increased to 55° C., maintained at this level for a further 30 min and subsequently reduced to approx. 20° C. Now the excess 1-butylamine (IIIb) is distilled off in a vacuum and collected in a cooled receiving vessel. In the flask there remains an almost colourless, viscous residue. This is heated together with 100 ml n-heptane to 70° C. After cooling to room temperature, the clear solution is separated by decanting from the base body and the solvent is distilled off. A light yellow liquid is obtained as distillation residue. This crude product is distilled in the fine vacuum (0.1 mbar). At 137 to 142° C., the compound Ib distils as a colourless, oily liquid with a purity of 98% by mol.

Yield: 20 g or 37% of the theoretical quantity.

$^1$H-NMR (DMSO-$d_6$, 250 MHz): δ=0.55-0.68 (t, 3H); 0.82-1.17 (m, 4H); 2.22-2.38 (m, 2H); 4.72-4.83 (q, 1H): 7.05-7.22 (m, 2H); 7.30-7.38 (m, 1H); 7.42-7.51 (m, 1H); 7.51-7.60 (m, 2H); 8.02-8.12 (m, 2H); $^{13}$C-NMR (DMSO-$d_6$, 63 MHz): δ=13.75; 19.27; 34.58; 34.65; 44.05; 44.18; 120.66; 122.80; 123.36; 123.45; 123.67; 125.41; 127.64; 129.81; 130.62; 130.71; 131.42; 132.96; 133.05; 133.61; 151.03; 151.16; $^{31}$P-NMR (DMSO-$d_6$): δ=79.09.

Details of the shift δ respectively in ppm.

3. 6-(N-isopropylamino)-(6H)-dibenz[c,e] [1,2]-oxaphosphorin Ic from (6H)-dibenz[c,e] [1,2]-oxaphosphorin-6-oxide IIa

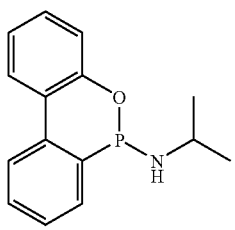

(Ic)

In a 1 litre flask, which is equipped with an agitator, a reflux cooler with an inert gas transfer pipe, a thermometer and also with a heating bath, a mixture of 150 ml toluene, 150 ml n-heptane and 1 mol (59 g; 86 ml) ispropylamine (IIIc) is heated to 45° C. Then 0.125 mol (27 g) 6H-dibenz[c,e] [1,2]-oxaphosphorin-6-oxide IIa which are ground into a powder are added. A further three portions of the starting substance IIa (respectively 0.125 ml or 27 g) are added at intervals of respectively 1 h, the temperature of the mixture being gradually increased to 50° C. Thereafter, 0.5 mol (30 g; 43 ml) of the amine (IIIc) are added and the obtained suspension is agitated for a further 1.5 h. The temperature is then increased to 54° C. and maintained at this level for 1.5 h. During this time, the base body is dissolved for the large part. After switching off the heating the reaction flask is kept under inert gas for 12 h, a viscous base body forming. Now the supernatant solution is decanted off and concentrated in a partial vacuum to approx. one third of its starting volume. There is added to the obtained pulp-like residue 150 ml n-heptane and this mixture is heated to approx. 50° C. After cooling the fine-grained suspension is filtered through a glass frit with the exclusion of moisture, and the filter cake (N-isopropylammonium-(2'-hydroxy-biphenyl-2-yl)-phosphinate; VIc) is rinsed twice with respectively 30 ml n-heptane. The solid material VIc can be decomposed by heating in a vacuum, the starting substances 6H-dibenz[c,e] [1,2]-oxaphosphorin-6-oxide IIa and isopropylamine and also water being released. The volatile components are now distilled off from the combined filtrates. An oily residue remains in which the product Ic has a proportion of approx. 93% by mol. This crude product is distilled in a fine vacuum (approx. 0.1 mbar). At 130 to 133° C., the compound Ic distils as a colourless, oily liquid. It is obtained with a purity of 98% by mol.

Yield: 40 g or 31% of the theoretical quantity.

$^1$H-NMR (DMSO-$d_6$, 250 MHz): δ=0.66-0.78 (m, 6H); 2.77-2.98 (m, 1H); 4.521-4.61 (q, 1H); 6.96-7.10 (m, 2H); 7.22-7.29 (m, 1H); 7.30-7.40 (m, 1H); 7.40-7.51 (m, 2H); 7.91-7.99 (m, 2H); $^{31}$P-NMR (DMSO-$d_6$): δ=75.14.

Details of the shift δ respectively in ppm.

4. 6-(N-allylamino)-(6H-dibenz[c,e] [1,2]-oxaphosphorin Id from 6H-dibenz[c,e] [1,2]-oxaphosphorin-6-oxide IIa

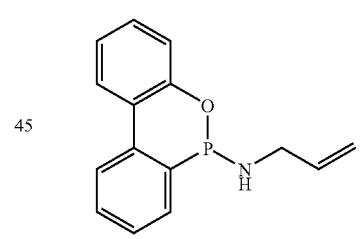

(Id)

In a 1 litre flask which is equipped with an agitator, a reflux cooler with an inert gas transfer pipe, a thermometer an also with a heating bath, a mixture of 150 ml toluene, 150 ml n-heptane and 1 mol (57 g; 75 ml) allylamine (IIId) is heated to 45° C. Then 0.125 mol (27 g) 6H-dibenz[c,e] [1,2]-oxaphosphorin-6-oxide IIa which is ground into a powder is added with agitation. Three further portions of the starting substance IIa are added at intervals of respectively one hour, the temperature being increased gradually to 50° C. Then the mixture is agitated for a further hour at unchanged temperature. Thereafter, 0.5 mol (30 g; 43 ml) allylamine (IIId) are added to the obtained suspension which is heated subsequent thereto to 55° C. The temperature is maintained for another 3 h at 55° C. and finally is lowered to approx 20° C., agitation taking place without interruption. After cooling, the reaction flask is maintained for 12 h under inert gas. Subsequently, the supernatant allylamine (IIId) is distilled off. The obtained fine-grained suspension is filtered through a glass frit with the exclusion of moisture, and the filter cake (N-alkylammonium-(2'-hydroxy-biphenyl-2-yl)-phosphinate; VId) is rinsed twice with respectively 30 ml n-heptane. The solid material VId can be decomposed by heating in a vacuum, the starting substances IIa and allylamine IIId being recovered and water being produced. The volatile components are now distilled off from the combined filtrates. The distillation residue is heated together with 150 ml n-heptane to 50° C., a milky-cloudy mixture being produced. From the latter, a solid base body gradually is deposited after cooling to room temperature, from which base body decanting takes place. The n-heptane is distilled off from the solution in a vacuum. An oily residue in which the product Id has a proportion of approx. 96% by mol remains. By means of a vacuum distillation, the purity of the product can be increased to 99% by mol. The compound Id distils at a pressure of approx. 0.1 mbar at 130 to 133° C.

Yield: 36 g or 28% of the theoretical quantity.

$^1$H-NMR (DMSO-$d_6$, 250 MHz): δ=3.26-3.40 (m, 2H); 4.85-4.97 (m, 3H); 5.53-5.70 (m, 1H) 7.16-7.28 (t, 2H); 7.37-7.44 (m, 1H); 7.44-7.56 (m, 1H); 7.57-7.73 (m, 2H); 8.03-8.14 (m, 2H); $^{31}$P-NMR (DMSO-$d_6$): δ=79.84.

Details of the shift δ respectively in ppm.

The invention claimed is:

1. A method of producing a dibenz[c,e] [1,2]-oxaphosphorin compound of the general formula I

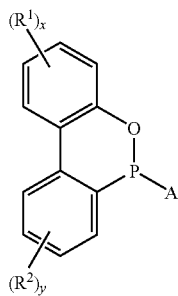

Formula I wherein a 6H-dibenz[c,e] [1,2]-oxaphosphorin-6-oxide of the general formula II

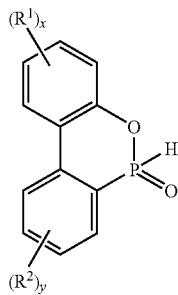

Formula II reacts with a compound of the general formula III

Z-A          Formula III to form the compound of formula I, wherein in the general formulae I, II and III respectively, independently of each other, x and y are 0, 1, 2, 3 or 4, $R^1$ and $R^2$ are the same or different and are selected from the group consisting of hydrogen, linear or branched $C_1$-$C_{22}$ alkyl, linear or branched $C_1$-$C_{22}$ O-alkyl or O-aryl, alkylsulphonyl, arylsulphonyl, thioaryl, thio-alkyl, linear or branched $C_3$-$C_{22}$ alkenyl, linear or branched $C_3$-$C_{22}$ alkynyl, linear or branched $C_1$-$C_{22}$ hydroxyalkyl, linear or branched $C_3$-$C_{22}$ alkoxycarbonylalkyl, $C_3$-$C_{12}$ cycloalkyl, $C_6$-$C_{14}$ aryl, $C_7$-$C_{22}$ aralkyl, $C_7$-$C_{22}$ alkylaryl, an optionally substituted piperidin-4-yl group and halogen atoms, A is a primary amine, a secondary amine substituted in a similar or mixed manner, a heterocyclic amine or a hydrazine compound, and Z is hydrogen, lithium, sodium or potassium.

2. The method of claim 1, wherein the amine and/or the hydrazine compound A contains up to 6 nitrogen atoms.

3. The method of claim 1, wherein the amine A represents a compound of the general formula IV

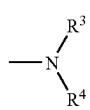

Formula IV wherein $R^3$ is hydrogen, linear or branched $C_1$-$C_{22}$ alkyl, linear or branched $C_1$-$C_{22}$ O-alkyl or O-aryl, alkylsulphonyl, arylsulphonyl, thioaryl, thioalkyl, linear or branched $C_3$-$C_{22}$ alkenyl, linear or branched $C_3$-$C_{22}$ alkynyl, linear or branched $C_1$-$C_{22}$ hydroxyalkyl, linear or branched $C_3$-$C_{22}$ alkoxycarbonylalkyl, $C_3$-$C_{12}$ cycloalkyl, $C_6$-$C_{14}$ aryl, $C_7$-$C_{22}$ aralkyl, $C_7$-$C_{22}$ alkylaryl or an optionally substituted piperidin-4-yl group, and $R^4$ is linear or branched $C_1$-$C_{22}$ alkyl, linear or branched $C_1$-$C_{22}$ O-alkyl or O-aryl, alkylsulphonyl, arylsulphonyl, thioaryl, thioalkyl, linear or branched $C_3$-$C_{22}$ alkenyl, linear or branched $C_3$-$C_{22}$ alkynyl, linear or branched $C_1$-$C_{22}$ hydroxyalkyl, linear or branched $C_3$-$C_{22}$ alkoxycarbonylalkyl, $C_3$-$C_{12}$ cycloalkyl, $C_6$-$C_{14}$ aryl, $C_7$-$C_{22}$ aralkyl, $C_7$-$C_{22}$ alkylaryl or an optionally substituted piperidin-4-yl group.

4. The method of claim 1, wherein the hydrazine compound A is a compound of the general formula V

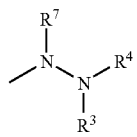

Formula V $R^3$ is hydrogen, linear or branched $C_1$-$C_{22}$ alkyl, linear or branched $C_1$-$C_{22}$ O-alkyl or O-aryl, alkylsulphonyl, arylsulphonyl, thioaryl, thioalkyl, linear or branched $C_3$-$C_{22}$ alkenyl, linear or branched $C_3$-$C_{22}$ alkynyl, linear or branched $C_1$-$C_{22}$ hydroxyalkyl, linear or branched $C_3$-$C_{22}$ alkoxycarbonylalkyl, $C_3$-$C_{12}$ cycloalkyl, $C_6$-$C_{14}$ aryl, $C_7$-$C_{22}$ aralkyl, $C_7$-$C_{22}$ alkylaryl or an optionally substituted piperidin-4-yl group, $R^4$ is linear or branched $C_1$-$C_{22}$ alkyl, linear or branched $C_1$-$C_{22}$ O-alkyl or O-aryl, alkylsulphonyl, arylsulphonyl, thioaryl, thioalkyl, linear or branched $C_3$-$C_{22}$ alkenyl, linear or branched $C_3$-$C_{22}$ alkynyl, linear or branched $C_1$-$C_{22}$ hydroxyalkyl, linear or branched $C_3$-$C_{22}$ alkoxycarbonylalkyl, $C_3$-$C_{12}$ cycloalkyl, $C_6$-$C_{14}$ aryl, $C_7$-$C_{22}$ aralkyl, C-$C_{22}$ alkylaryl or an optionally substituted piperidin-4-yl group and $R^7$ is hydrogen, linear or branched $C_1$-$C_{22}$ alkyl, linear or branched $C_1$-$C_{22}$ O-alkyl or O-aryl, alkylsulphonyl, arylsulphonyl, thioaryl, thioalkyl, linear or branched $C_3$-$C_{22}$ alkenyl, linear or branched $C_3$-$C_{22}$ alkynyl, linear or branched $C_1$-$C_{22}$ hydroxyalkyl, linear or branched $C_3$-$C_{22}$ alkoxycarbonylalkyl, $C_3$-$C_{12}$ cycloalkyl, $C_6$-$C_{14}$ aryl, $C_7$-$C_{22}$ aralkyl, $C_7$-$C_{22}$ alkylaryl or an optionally substituted piperidin-4-yl group.

5. The method of claim 1, wherein the reaction is implemented in an inert aprotic solvent.

6. The method of claim 1, wherein the compound of formula III is used in a molar material quantity ratio to the oxaphosphorin oxide of formula II from 1:1 to 50:1.

7. The method of claim 1, wherein the reaction temperature is between 10 and 200° C.

8. The method of claim 1, wherein a by-product which is produced during the reaction of the general formula VI

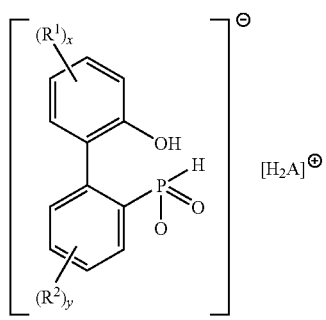

Formula VI is separated from the reaction mixture, $R^1$, $R^2$, A, x and y having the above-indicated meaning, and the oxaphosphorin oxide of formula II is recovered therefrom by thermolytic decomposition and the compound of formula III is recovered by water splitting.

9. The method of claim 8, wherein the thermolysis is implemented at temperatures between 80 and 280° C.

10. The method of claim 8, wherein the thermolysis is implemented at reduced pressure.

11. The method of claim 8, wherein at least the oxaphosphorin oxide of formula II is supplied again to the reaction.

12. The method of claim 5, wherein the solvent is selected from the group consisting of ligroin, benzene, toluene, xylene, hexane, cyclohexane, dimethylformamide, dimethylacetamide, sulpholane, acetonitrile, dioxane, di-n-butylether, 1,2-dichloroethane, dimethylsulphoxide, acetic acid ester, methylethylketone, nitrobenzene, nitromethane, tetrahydrofuran, chloroform, trichloroethane, and mixtures thereof.

13. The method of claim 6, wherein the ratio is 1:1 to 20:1.

14. The method of claim 7, wherein the reaction temperature is between 20 and 120° C.

15. The method of claim 9, wherein the temperature is between 100 and 200° C.

16. The method of claim 10, wherein the thermolysis is implemented at a pressure less than 100 mbar.

* * * * *